US00RE42394E

(19) United States
(12) Reissued Patent
Mudge

(10) Patent Number: US RE42,394 E
(45) Date of Reissued Patent: May 24, 2011

(54) FUNGICIDAL COMPOSITIONS FOR THE ENHANCEMENT OF TURF QUALITY

(75) Inventor: Laurence C. Mudge, Camden, SC (US)

(73) Assignee: Bayer CropScience Inc., Research Triangle Park, NC (US)

(21) Appl. No.: 10/849,509

(22) Filed: May 19, 2004

Related U.S. Patent Documents

Reissue of:
(64) Patent No.: 5,599,804
Issued: Feb. 4, 1997
Appl. No.: 08/415,934
Filed: Apr. 3, 1995

(51) Int. Cl.
*A01N 43/58* (2006.01)
*A01N 57/18* (2006.01)
*A01N 59/26* (2006.01)

(52) U.S. Cl. ..... 514/141; 514/410; 424/601; 424/602; 424/605; 424/606

(58) Field of Classification Search ..... 514/141
See application file for complete search history.

(56) References Cited

U.S. PATENT DOCUMENTS

| | | | | | |
|---|---|---|---|---|---|
| 2,129,013 | A | | 9/1938 | Linstead et al. | 260/314 |
| 2,214,454 | A | | 9/1940 | Dent | 260/314 |
| 2,276,860 | A | | 3/1942 | Niemann et al. | 260/314 |
| 2,452,606 | A | | 11/1948 | Roselle | 106/289 |
| 2,460,779 | A | | 2/1949 | Brouillard et al. | 260/314.5 |
| 2,460,783 | A | | 2/1949 | Lecher et al. | 260/314.5 |
| 2,471,794 | A | | 5/1949 | Sumner | 260/314.5 |
| 2,485,167 | A | | 10/1949 | Rintelman | 260/314.5 |
| 2,485,168 | A | | 10/1949 | Rintelman | 260/314.5 |
| 2,556,729 | A | | 6/1951 | Bridgeton | 260/314.5 |
| 2,613,128 | A | | 10/1952 | Baumann et al. | 8/28 |
| 3,379,610 | A | | 4/1968 | Lyon et al. | 167/22 |
| 3,632,328 | A | | 1/1972 | Gaskin et al. | 71/3 |
| 3,950,265 | A | | 4/1976 | Albrecht et al. | 252/311 |
| 4,139,616 | A | | 2/1979 | Ducret et al. | 424/222 |
| 4,394,316 | A | | 7/1983 | Chao | 260/429 |
| 4,698,334 | A | | 10/1987 | Horriere et al. | 514/141 |
| 4,806,445 | A | | 2/1989 | Horriere et al. | 514/141 |
| 4,956,183 | A | | 9/1990 | Miki et al. | 424/630 |
| 5,171,853 | A | | 12/1992 | Thorp et al. | 536/27 |
| 5,206,228 | A | * | 4/1993 | Collins | 514/141 |
| 5,336,661 | A | * | 8/1994 | Lucas | 504/126 |
| 5,350,843 | A | | 9/1994 | Itoh et al. | 540/138 |
| 5,380,842 | A | | 1/1995 | Itoh et al. | 540/138 |
| 5,665,672 | A | * | 9/1997 | Lucas | 504/126 |

FOREIGN PATENT DOCUMENTS

| | | | |
|---|---|---|---|
| DE | 2412324 | * | 9/1975 |
| DE | 2511077 | | 9/1976 |
| EP | 0 419 915 A2 | | 9/1990 |
| FR | 1-562-940 | | 3/1969 |
| JP | 1-157904 | | 7/1982 |
| JP | 57-034781 | | 7/1982 |
| JP | 82034781 | | 7/1982 |
| JP | 63112701 | * | 5/1988 |
| JP | 1-157904 | | 6/1989 |
| JP | 02138376 | * | 5/1990 |
| JP | 03221576 | * | 9/1991 |
| JP | 6-73397 | | 3/1994 |
| JP | 06321711 | * | 11/1994 |
| PL | 103345 | * | 5/1979 |
| PL | 103345 | | 6/1979 |

OTHER PUBLICATIONS

Fenn et al, Studies on the in vitro and in vivo antifungal acitivity of fosetyl-AI and phosphorous acid, Phytopathology, 74 (5), pp. 606-611.*

Gullino et al. (Chemical control of dollar spot and brown patch of turfgrass in Italy, Mededelingen—Faculteit Landbouwkundige en Toegepaste Biologische Wetenschappen, Universiteit Gent, 1995, 60, 2b Proceedings, 47th International Symposium on Crop Protection, pt. 2, 1995, 367-70.*

Printout of http://www2.siri.org/msds/f2/bzz/bzzsc.html, for ingredients in Rohm and Haas Co.'s FORE.TM. Fungicide, 62440 (Jul. 24, 1991).*

FORE Specimen Label, Apr. (1985).

CHIPCO Specimen Label, (1992).

S. Lessage, *Reduction of the Formation of Ethylenethiourea from Ethylenebis (dithiocarbamates) by Cupric Ions in Aqueous Media,* J. Agric. Food Chem. 28(4), pp. 787-790 (1980).

A. Stevenson, *Fungicidal Compositions,* Patent Journal, p. 39 (Jul. 26, 1967).

N. M. Bigelow et al., *Phthalocyanine Pigments,* The Chemistry of Synthetic Dyes and Pigments, pp. 577-606 (1960).

W. S. Struve, *Phthalocyanine Dyes,* The Chemistry of Synthetic Dyes and Pigments, pp. 607-624 (1960).

T. Ostmeyer, *The Color Green,* Golf Course Management, pp. 40-44 (Aug. 1994).

M. E. Fenn et al., *Studies on the In Vitro and In Vivo Antifungal Activity of Fosetyl-Al and Phosphorous Acid,* Phytopathology 74, No. 5, pp. 606-611 (1984).

S. G. Martin et al., *Pathogenicity of Rhizoctonia zeae on Tall Fescue and Other Turfgrasses,* Plant Disease 67:676 (1983).

S. G. Martin et al., *Characterization and Pathogenicity of Rhizoctonia spp. and Binucleate Rhizoctonia-like Fungi from Turfgrass Species,* Phtyphathology 74:170 (1984.).

L. T. Lucas, *Diseases of Warm-Season Grasses,* N.C. Agri. Ext. Ser. AG-360 (reprinted) (1987).

L. B. McCarthy et al., *Gaeumannomyces Graminis Associated with Spring Dead Spot of Bermudagrass in South Eastern United States,* Plant Disease 73:659 (1989).

L. T. Lucas, *Diseases of Bentgrass on High-Sand-Content Golf Greens,* Plant Pathology Turfgrass Disease Information Note No. 4 (1990).

L. B. McCarthy et al., *Regrowth of Bermudagrass Infected with Spring Dead Spot Following Low Temperature Exposure,* Crop Science 31:182 (1991).

(Continued)

*Primary Examiner* — Alton N Pryor
(74) *Attorney, Agent, or Firm* — Lerner, David, Littenberg, Krumholz & Mentlik, LLP

(57) ABSTRACT

Fungicidal compositions for the protection of turfgrass against crown and root rot are disclosed. The compositions comprise, as the active material, (a) a first active agent selected from the group consisting of (i) a monoester salt of a phosphorous acid (preferably aluminum ethyl phosphite), and (ii) phosphorous acid or an alkali or alkali earth metal salt thereof; and (b) a benzoporphyrin compound. Preferred compositions comprise 1 part by weight of the first active agent, and between about 0.01 and about 0.1 parts by weight of the benzoporphyrin compound.

34 Claims, No Drawings

OTHER PUBLICATIONS

L. T. Lucas, *Disease-Like Problems on Turfgrasses in North Carolina,* Plant Pathology Turfgrass Disease Information Note No. 5 (1992).

L. T. Lucas, *Diseases of Tall Fescue,* Plant Pathology Turfgrass Disease Information Note No. 6 (1992).

L. T. Lucase, *Long-Term Turf management Practices for Prevention of Turf Diseases,* Plant Pathology Turfgrass Information Note No. 7 (1992).

L. B. McCarthy et al., *Spring Dead Spot Occurrence in Bermudagrass Following Fungicide and Nutrient Applications,* Hort. Science 27:1092 (1992).

Rule 132 Declaration of Leon T. Lucas and Laurence C. Mudge, filed in U.S. Appl. No. 08/003632, Jan. 11, 1994 (U.S. Pat. No. 5,336,661).

Supplemental Rule 132 Declaration of Leon T. Lucas and Laurence C. Mudge , Filed in U.S. Serial No. 08/003632, Mar. 25, 1994 (U.S. Pat. No. 5,336,661).

Published photographs of plots treated with combination of treatments taken by Leon T. Lucas, Jan. 11, 1994 (Appendix 1 of above Rule 132 Declarations).

L.T. Lucas, *1993 Field Plot Results indicating Synergistic Interaction of Chipco Aliette (Fosethyl-Al) and Mancozeb,* Plant Pathology Department, N.C. State University, Sep. 15, 1993. (Appendix 2 of above Rule 132 Declarations).

H. Couch et al., *Synergistic and antagonistic interactions of fungicides against Pythium aphanidermatum on perennial ryegrass,* Crop Protection, vol. 10, Oct. 1991, pp. 386-390. (Appendix 3 of above Rule 132 Declarations).

H. Couch, *Aliette 80 WDG/Fore 80 WP Synergy in the control of Rhizoctonia Blight (in vivo) Trial 2,* Virginia Polytechnic Inst. & State University, Oct. 1993. (Appendix 4 of above Rule 132 Declarations).

Article, "New Fungicide Combination Sets Record Sales". (Appendix 5 of above Rule 132 Declarations).

Article, "Rhone Polenc", Turf North, May 1993. (Appendix 5 of above Rule 132 Declarations).

Article, "North Carolina State Study Claims Mix Controls Summer Stress", Golf Course News, May 1993. (Appendix 5 of above Rule 132 Declarations).

Article, "For the Asking", Southern Golf, May/Jun. 1993, p. 28. (Appendix 5 of above Rule 132 Declarations).

Article, "Tank Mix Offered for Summer Stress Complex", Golf Course Management, Apr. 1993, p. 130. (Appendix 5 of above Rule 132 Declarations).

L.T. Lucas, "Summer Stress Complex", N.C. State University Presentation, 1992. (Appendix 6 of above Rule 132 Declarations).

"Chipco Tips" Information Pamphlet, 1993. (Appendix 7 of above Rule 132 Declarations).

"Summer Bentgrass Decline" Pamphlet. (Appendix 8 of above Rule 132 Declarations).

* cited by examiner

FUNGICIDAL COMPOSITIONS FOR THE ENHANCEMENT OF TURF QUALITY

Matter enclosed in heavy brackets [ ] appears in the original patent but forms no part of this reissue specification; matter printed in italics indicates the additions made by reissue.

FIELD OF THE INVENTION

The present invention relates to methods and compositions for the enhancement of turf quality and the control or crown and root rot in turfgrass, and more particularly to synergistic combinations of fungicides useful therefore.

BACKGROUND OF THE INVENTION

Crown and root rot is a serious disease of turfgrasses, especially highly maintained turfgrasses as found in lawns, golf courses, nursery crops, and other landscape architecture applications. Current techniques for controlling this disease are not entirely satisfactory, and there is a continuing need for new treatments thereof.

U.S. Pat. No. 4,698,334 to Horriere et al. and U.S. Pat. No. 4,806,445 to Horriere et al. propose fungicidal compositions based on alkyl phosphites in combination with various contact fungicities such as Mancozeb. These compositions are useful for treating mildew in vines. U.S. Pat. No. 4,139,616 to Ducret et al. describes fungicidal compositions based on alkyl phosphites. None of these references relate to the treatment of turfgrasses.

U.S. Pat. No. 5,336,661 to Lucas discloses methods of enhancing turf quality of bentgrass using compositions comprising a mixture of a monoester salt of a phosphorous acid, and an ethylenebisdithiocarbamate contact fungicide.

High quality, healthy turfgrass is essential to the golfing industry. Accordingly, there remains a need in the art for fungicidal compositions which enhance turf quality and protect against crown and root rot in turfgrass to provide high quality, healthy turfgrass.

SUMMARY OF THE INVENTION

As a first aspect, the present invention provides a fungicidal composition for enhancing the quality of turfgrass and protecting against crown and root rot. The compositions comprise a synergistic combination of:

(a) a first active agent selected from the group consisting of (i) a monoester salt of a phosphorous acid of Formula (I):

(I)

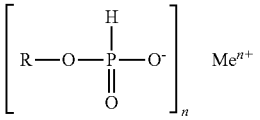

wherein:

R is an alkyl radical having 2 to 4 carbon atoms,

Me is an alkali metal, alkaline earth metal, or aluminum atom, and n is a whole number from 1 to 3 equal to the valence of Me: and (ii) phosphorous acid or an alkali or alkali earth metal salt thereof: and (b) a benzoporphyrin compound.

As a second aspect, the present invention provides a method of enhancing turf quality and protecting against crown and root rot. The method comprises applying (a) a first active agent selected from the group consisting of (i) a monoester salt of a phosphorous acid of Formula (I) above, and (ii) phosphorous acid or an alkali or alkali earth metal salt thereof, and (b) a benzoporphyrin compound.

The compounds are applied in an amount effective to enhance turf quality and/or protect against crown and root rot. In one embodiment, the active agents applied consist essentially of the monoester salt and the benzoporphyrin compound.

The benzoporphyrin compounds useful in the method of the present invention include substituted and unsubstituted benzoporphyrins and derivatives thereof. Suitable benzoporphyrins include tetrabenzoporphyrine, alkyl-substituted benzoporphyrins, halo-substituted benzoporphyrins, and the like. According to one embodiment, the benzoporphyrin is a coordination complex of the Formula $L_1L_2$—$X_1X_2$—$L_3L_4$, wherein $X_1$ and $X_2$ are each H or $X_1$ and $X_2$ together are a transition metal, and $L_1$, $L_2$, $L_4$, and $L_4$ are each substituted or unsubstituted isoindole groups, and wherein $L_1$, $L_2$, $L_3$, and $L_4$ are covalently joined to one another. In one preferred coordination complex, $L_1$, $L_2$, $L_3$, and $L_4$ together form a ligand of Formula (II)

(II)

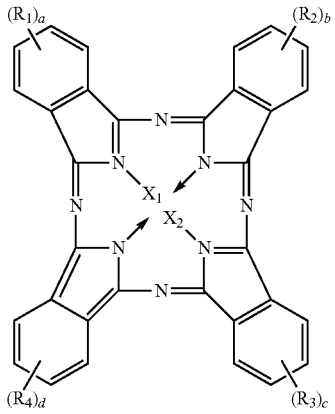

wherein a, b, c, and d are each independently selected from positive integers 0-4, and $R_1$, $R_2$, $R_3$, and $R_4$ are each independently selected from the group consisting of H, halogen, $C_{1-20}$ substituted or unsubstituted, saturated or unsaturated, linear, branched or cyclic alkyl, alkoxy, alkylamino, alkylthio, onium, sulphonium, sulphate, and carboxylate.

The foregoing and other aspects of the present invention are explained in detail in the detailed description set forth below.

DETAILED DESCRIPTION OF THE INVENTION

The methods and compositions described herein are useful for improving turf quality and color in turfgrasses. In addition, the methods and compositions described herein are useful for treating crown and root rot in turfgrass. Crown and root rot, which causes a decline in turfgrass quality during hot, wet weather, is a disease complex apparently caused by Pythium species and Rhizoctonia species in combination with environmental and management stresses.

The first active agent is selected from the group consisting of monoester salts of phosphorous acid and phosphorous acid or alkali or alkali earth metal salts thereof. Monoester salts of phosphorus acids useful for carrying out the present invention, as given in Formula (I) above, are known. See, e.g., U.S. Pat. No. 4,139,616 to Ducret et al. U.S. Pat. No. 4,698,334 to Horriere et al. and U.S. Pat. No. 4,806,445 to Horriere et al. (the disclosures of all U.S. patents cited herein are to be incorporated herein by reference). Examples include calcium ethyl phosphite, sodium ethyl phosphite, aluminum ethyl phosphite, magnesium isopropyl phosphite, calcium isopropyl phosphite, aluminum isopropyl phosphite, magnesium ethyl phosphite, magnesium isobutyl phosphite, magnesium sec-butyl phosphite, calcium isobutyl phosphite, aluminum N-butyl phosphite, aluminum sec-butyl phosphite, and aluminum isobutyl phosphite. Most preferred is aluminum ethyl phosphite also called aluminum Iris (0-ethyl phosphonate)).

Alternatively, the first active agent may be phosphorous acid or an alkali or alkali earth metal salt thereof. Suitable alkali or alkali earth metal salts include, for example, lithium, sodium, polassiu, rubidium, cesium, beryllium, magnesium, calcium, strontium, and barium salts of phosphorous acid. The sodium, potassium and calcium salts or phosphorous acid are currently preferred.

Benzoporphyrin compounds are the preferred class of porphine compounds and derivatives thereof, which are useful in the methods of the present invention. Examples of useful porphine compounds include substituted and unsubstituted porphines and derivatives thereof. Suitable derivatives of porphines include substituted and unsubstituted porphyrins. The porphyrins may be benzoporphyrins such as tetrabenzoporphyrins, alkyl-substituted benzoporphyrins, halo-substituted benzoporphyrins, and the like. According to one embodiment, the benzoporphyrin is a coordination complex of the Formula $L_1L_2$—$X_1X_2$—$L_3L_4$, wherein $X_1$ and $X_2$ are each H or $X_1$ and $X_2$ together are a metal selected from the group consisting of alkali metals, alkali earth metals and transition metals, and $L_1$, $L_2$, $L_3$, and $L_4$ are each substituted or unsubstituted isoindole groups, and wherein $L_1$, $L_2$, $L_3$, and $L_4$ are covalently joined to one another (e.g., through a nitrogen or carbon atom, preferably a nitrogen atom). As will be apparent, they are covalently joined as a cyclic structure, i.e. —$L_1$—$L_3$—$L_4$—cy, where 0 means $L_4$ is covalently joined to $L_1$. Preferably, $X_1$ and $X_2$ together are a transition metal from Groups IB and VIIIB. The isoindole groups represented by $L_1$, $L_2$, $L_3$, and $L_4$ may be unsubstituted, or alternatively, they may be each independently substituted from 1 to 4 times with a substituent selected from the group consisting of halogen, $C_{1-20}$ substituted or unsubstituted, saturated or unsaturated, linear, branched or cyclic alkyl, alkoxy, alkylamino, alkylthio, onium, sulphonium, sulphate, and carboxylate.

In one preferred embodiment of the coordination complex of $L_1L_2$—$X_1X_2$—$L_3L_4$, $L_1$, $L_2$, $L_3$, and $L_4$ together form a ligand of Formula (II)

(II)

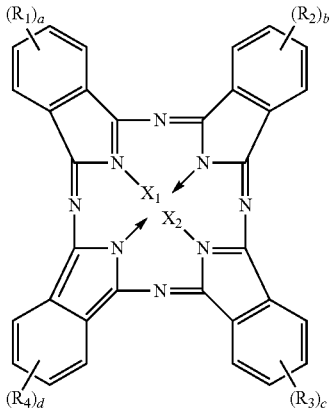

wherein a, b, c, and d are each independently selected from positive integers 0-4, and $R_1$, $R_2$, $R_3$, and $R_4$ are each independently selected from the group consisting of H, halogen, $C_{1-20}$ substituted or unsubstituted, saturated or unsaturated, linear, branched or cyclic alkyl, alkoxy, alkylamino, alkylthio, onium, sulphonium, sulphate, and carboxylate.

Examples of suitable benzoporphyrins of the coordination complex $L_1L_2$—$X_1X_2$—$L_3L_4$ include phthalocyanine dyes. Suitable phthalocyanine dyes may be metal-free phthalocyanines, or metal phthalocyanines. The metal of metal phthalocyanines may be selected from alkali metals, alkali earth metals and transition metals, with transition metals being preferred. Examples of suitable metals include but are not limited to, lithium, sodium, potassium, rubidium and cesium from the alkali metal family; berillium, magnesium, calcium, strontium, barium, and radium from the alkali earth metal family; and copper, silver, gold, zinc, cadmium, mercury, scandium, yittrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nichel, palladium, and platinum from the transition metal family. Copper, nickel, cobalt, iron and zinc phthalocyanine dyes are particularly preferred in the methods of the present invention.

Phthalocyanine dyes which are useful in the methods of the present invention include subsituted and unsubstituted dyes. Suitable substituted phthalocyanine dyes may be metal-tree phthalocyanines, or metal phthalocyanines, and may be substituted from 1 to 4 times on each isoindole group independently. Examples of suitable substituents for the isoindole groups of phthalocyanine dyes include but are not limited to, halogens, substituted or unsubstituted, saturated or unsaturated, linear, branched or cyclic alkyl, alkoxy, alkylamino, alkylthio, onium, sulphonium, sulphate, and carboxylate. Suitable phthalocyanine dyes are commercially available and include but are not limited to Pigment Blue 16, Vat Blue 29. Pigment Blue 15, Heliogen Green GG, Ingrain Blue 14, Ingrain Blue 5, Ingrain Blue 1, Pigment Green 37, and Pigment Green 7. In one preferred embodiment, the phthalocyanine dye is Pigment Blue 15. In another preferred embodiment, the phthalocyanine dye is any phthalocyanine dye other than Pigment Blue 15.

Synergistic combinations of the foregoing two active ingredients (the two together being referred to herein as the "active material") are, in general, 1 part by weight of the compound of Formula (I) above in combination with from 0.01 to 0.1, preferably 0.04 to 0.05. parts by weight of the benzoporphyrin compound. More preferably, the active material includes 1 part by weight of the compound of Formula (I) above in combination with from 0.01 to 0.1 parts by weight of the benzoporphyrin compound. A particularly preferred combination is 1 part by weight of the compound of Formula (I) above in combination with from 0.04 to 0.05 parts by weight of Pigment Blue 15.

The synergistic combinations according to the invention may be used with advantage in admixture with one another or with other known fungicides, such as basic salts or hydroxides of copper (oxychloride, oxysulphate), (tetrahydro)phthalimides (Captan, Captafol, Folpel), methyl 1-(butylcarbamoyl)-2-benzimidazolecarbamate (Benomyl), thiophanates such as dimethyl (1,2-phenylene)bis(iminocarbonothioyl)bis(carbamate) (Thiophanate-methyl), tetrachloroisophthalonitrile (Chlorothalonil), 3-(3,5-dichlorophenyl)-N-(1-methylethyl)-2,4-dioxo-1-imidazolidine carboxamide (Iprodione), 1-[2-(2,4dichlorophenyl)4-propyl-1,3-dioxolan-2-yl methyl]-1H-1,2,4-triazole (Propiconazole) 1-(4-chlorophenoxy)-3,3-dimethyl-1(1H-1,2,4-triazol- 1-yl)-2-butanone (Triadimafon) or other fungicides, either to complete the range of activity of the compounds according to the invention or to increase their persistence.

The synergistic combinations according to the invention may also be mixed with other fungicidal, anti-mildew phosphorus derivatives, especially 2-hydroxy-1,3,2-dioxaphospholanes, β-hydroxy ethyl phosphites and phosphorous acid and its salts.

For their practical application, the active ingredients in the synergistic combinations are used as part of a formulated product which, as a rule, contains a support and/or a surfactant in addition to the active material according to the invention.

In the context of the invention, a support is an organic or mineral, natural or synthetic material with which the active material is associated to facilitate its application to plants, seeds or soil, or its transportation and/or handling. The support can be solid (clays, natural or synthetic silicates. resins, waxes, solid fertilizers) or fluid (water, alcohols, ketones, petroleum fractions. chlorinated hydrocarbons, liquefied gases).

The surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions according to the invention can be prepared in the form of wettable powders, soluble powders, dusting powders, granulates, solution, emulsifiable concentrates, emulsions, suspended concentrates and aerosols.

The wettable powders according to the invention can be prepared in such a way that they contain from 20 to 95% by weight of the active material, and they normally contain, in addition to a solid support, from 0 to 5% by weight of a wetting agent, from 3 to 10% by weight of a dispersant and, when necessary, from 0 to 10% by weight of one or more stabilizers and/or other additives, such as penetration agents, adhesives or anti-lumping agents, colorants, etc.

One example of the compositions of a wettable powder is given in Table 1 below:

TABLE 1

| Compound | % by wt. |
|---|---|
| active material | 80 |
| sodium lignosulphonate (deflocculant) | 5 |
| anionic wetting agent | 1 |
| antilumping silica | 5 |
| kaolin (filler) | 9 |

Powders soluble in water are obtained by mixing from 20 to 95% by weight of the active material, from 0 to 10% of an antilumping agent, the remainder being a hydrosoluble filler mainly a salt.

An example of a composition of the present invention as a soluble powder is given in Table 2 below:

TABLE 2

| Compound | % by wt. |
|---|---|
| active material | 70 |
| anionic wetting agent | 0.5 |
| antilumping silica | 5 |
| sodium sulfate (soluble filler) | 24.5 |

Aqueous dispersions and emulsions, for example compositions obtained by diluting with water a wettable powder or an emulsifiable concentrate according to the invention, are included within the general scope of the invention. These emulsions can be of the water-in-oil type or of the oil-in-water type, and can have a thick consistency resembling that of a "mayonnaise".

The compositions according to the invention can contain other ingredients, for example protective colloids, adhesives or thickeners, thixotropic agents, stabilizers or sequestrants, as well as other active materials known to have pesticidal properties, especially acaricides or insecticides.

The present invention can be practiced with all turfgrasses, including cool season turfgrasses and warm season turfgrasses. Examples of cool season turfgrasses are Bluegrasses (Poa L.), such as Kentucky Bluegrass (Poa pratensis L.), Rough Bluegrass (Poa trivialis L.), Canada Bluegrass (Poa compressa L.), Annual Bluegrass (Poa annua L.), Upland Bluegrass (Poa glaucantha Gaudin), Wood Bluegrass (Poa nemoralis L.). and Bulbous Bluegrass (Poa bulbosa L.); the Bentgrasses and Redtop (Agrostis L.), such as Creeping Bentgrass (Agrostis palustris Huds.), Colonial Bentgrass (Agrostis tenius Sibth.), Velvet Bentgrass (Agrostis canina L.), South German Mixed Bentgrass (Agrostis L.), and Redtop (Agrostis alba L.); the Fescues (Festuca L.), such as Red Fescue (Festuca rubra L.). Chewings Fescue (Festuca rubra var. commutata Gaud.), Sheep Fescue (Festuca ovina L.), Hard Fescue (Festuca ovina var. duriuscula L. Koch), Hair Fescue (Festuca capillata Lam.). Tall Fescue (Festuca arundinacea Schreb.), Meadow Fescue (Festuca elanor L.); the Ryegrasses (Lolium L.), such as Perennial Ryegrass (Lollium perenne L.), Italian Ryegrass (Lolium multiflorum Lam.); the Wheatgrasses (Agropyron Gaertn.), such as Fairway Wheatgrass (Agropyron cristatum (L.) Gaertn.), Western Wheatgrass (Agropyron smithii Rydb.). Other cool season turfgrasses include Beachgrass (Ammophila Host.), Smooth Brome (Bromus inermis Leyss.), Timothy (Phleum L.). Orchardgrass (Dactylis glomerata L.), Crested Dog's-Tail (Cynosurus cristatus L.). Examples of warm season turfgrasses are the Bermudagrasses (Cynodon L. C. Rich), Zoysiagrasses (Zoysia Willd.), St. Augustinegrass (Stenotaphrum secundatum (Wait.) Kuntze), Centipedegrass (Eremochioa ophiuroides (Munro.) Hack.), Carpetgrass (Axonopus Beauv.), Bahiagrass (Paspalum notalum Flugge.), Kikuyugrass (Pennisetum clandestinum Hochst. ex Chiov.), Buffalograss (Buchloe dactyloides (Nutt.) Engelm.), Blue Grama (Bouteloua gracilis (H.B.K.) Lag. ex Steud.), and Sideoats Grama (Bouteloua curtipendula (Michx. Torr.). Cool season turfgrasses are preferred. More preferred is Bluegrass, Bentgrass and Redtop, Fescue, and Ryegrass. Bentgrass is most preferred.

The active materials are, in general, applied to turfgrass either together or separately by spraying a liquid formulation (e.g., an aqueous formulation, including emulsions, or an oil-based formulation) thereof on the turfgrass. The ethylenebisdithiocarbamate contact fungicide is typically applied in an amount of from 10 to 25 pounds per acre (about 10 to 25 Kilograms per Hectare), more preferably in an amount of from 15 to 20 pounds per acre (about 15 to 20 Kg per hectare), and still more preferably in an amount of from 17 to 18 pounds per acre (about 17 to 18 Kg per Hectare). The compound of Formula (I) is, in general, applied in an amount of from about 5 to 17 pounds per acre.

The following examples are provided to illustrate the present invention, and should not be construed as limiting thereof.

EXAMPLES 1-3

These examples were carried out to identify fungicide and combinations thereof which will improve turf quality and color, and have activity against crown and root rot and brown patch. Fungicides were evaluated on a one-year-old stand of the bentgrass cultivar "Penncross" planted in Raleigh, N.C., U.S.A. The bentgrass was planted in native soil and maintained under conditions similar to a golf green with a mowing height of 0.635 cm (.25 inches). The fungicides which have activity against Pythium species include KOBAN™ (active ingredient: etridiazole) obtained from Grace-Sierra, ALIETTE™ (active ingredient: fosetyl-Al) obtained from Rhone-Poulenc. and SUBDUE™ (active ingredient: metalaxyl) obtained from Ceba-Giegy. The fungicides which have activity against Pythium and Rhizoctonia species is FORE™ (active ingredient: mancozeb also including Pigment Blue 15) obtained from Rhom and Haas, MANZATE™ (active ingredient: mancozeb) obtained from DuPont, LESCO MN80™ (active ingredient: mancozeb) obtained from Lesco, PENCOZEB DF 75™ (active ingredient: mancozeb) obtained from Elf Atochem, PROTECT DG 80™ (active ingredient: mancozeb) obtained from W. A. Cleary, and DITHANE™ (active ingredient: mancozeb) obtained from Rhom and Haas.

The fungicides were applied separately and in combination at labelled rates to 1.5 m×1.5 m (5 ft×5 ft) plots of bentgrass prior to evidence of any decline in turf quality due to crown and root rot. A $CO_2$ backpack sprayer was used to apply the fungicide treatments at (30 lbs psi) using TEEJET™ 8004 nozzles to apply 9.5 liters (2.5 gallons) of fungicide dilutions per 93 square meters (1000 sq ft). The fungicides were initially applied and subsequently reapplied according to a 14 day schedule. In some experiments, an electrical pump sprayer was used to apply the treatments at 30 psi using a Teejet 8004 nozzle.

Turf quality, color and percent disease ratings were recorded weekly, based on a scale from 1-9, with 9 being ideal turf quality and color and 1 being all turf dead. The percent disease ratings were calculated based on the percent of area in each plot showing symptoms of brown patch. Turf quality and color ratings were used as an indicator of the health of the bentgrass and the amount of decline associated with crown and root rot. Pythium and Rhizoctonia species of fungi were isolated from the bentgrass in the experiment during the test period.

Table 1 below indicates that an improvement in turf quality and color was observed from application of ALIETTE™+FORE™ (treatment #4), with a turf quality of 7.5 and a turf color of 7.8 with 9 being ideal. The combination of ALIETTE™+MANZATE™ had a lower turf quality rating of 6.8 and a turf color of 7.0.

TABLE 1

ALIETTE ™/FORE ™ Interaction

| Trt. No. | Pesticide Name | Formu. | LBai/A | Turf Quality | Turf Color | % Brown Patch | Disease Control |
|---|---|---|---|---|---|---|---|
| 01 | CHECK | — | — | 4.5 | 5.3 | 50.0 | 0 |
| 02 | ALIETTE ™ | WDG 80 | 8.712 | 6.5 | 6.8 | 0 | 100.0 |
| | CHP26019 | WDG 50 | 2.72 | | | | |
| 03 | ALIETTE ™ | WDG 80 | 8.712 | 6.8 | 7.0 | 0 | 100.0 |
| | MANZATE | WP 70 ™ | 16.34 | | | | |
| 04 | ALIETTE ™ | WDG 80 | 8.712 | 7.5 | 7.8 | 0 | 100.0 |
| | FORE ™ | WP 80 ™ | 17.42 | | | | |
| 05 | FORE ™ | WDG 80 | 17.42 | 6.8 | 7.0 | 2.5 | 91.7 |
| 06 | ALIETTE ™ | WDG 80 | 8.712 | 5.0 | 5.8 | 26.3 | 38.0 |
| 07 | ALIETTE ™ | WDG 80 | 4.356 | 6.8 | 7.5 | 0 | 100.0 |
| | FORE ™ | WP 80 ™ | 8.712 | | | | |
| | LSD (0.05) = | | | 1.0 | .8 | 9.1 | 23.5 |
| | STANDARD DEVIATION = | | | .7 | .5 | 6.2 | 16.1 |
| | COEFF. OF VARIABILITY = | | | 10.8 | 8.2 | 71.2 | 19.9 |

Table 2 below indicates that similar results were observed in a second test. The data demonstrate that ALIETTE™+FORE™ (treatment #8) gave better turf quality of 7.8 and 8.0 than ALIETTE™+mancozeb+AURAGREEN™ (another type of green dye) (treatment #5) of 7.0 and 7.3. The combination of the experimental formulation of ALIETTE™ and the blue pigment EXP 10622)+mancozeb (treatment#10) gave higher turf quality ratings of 7.5 and 8.0 than treatment #5. and ratings as high as the ratings for ALIETTE™+FORE™.

TABLE 2

ALIETTE ™/FORE ™ Interaction

| Trt. No. | Pesticide Name | Formu. | LBai/A | Application Type | Phyto rating | Turf Qual. | % Brown Patch | Turf Qual. | Turf Color | % Brown Patch |
|---|---|---|---|---|---|---|---|---|---|---|
| 01 | CONTROL | — | — | — | 1.0 | 5.0 | 25.0 | 5.3 | 6.3 | 15.0 |
| 02 | NCAD 1 | SG 100 | 0.545 | 14 DAY | 1.0 | 4.8 | 21.3 | 5.0 | 7.5 | 16.3 |
| 03 | NCAD 1 | SG 100 | 0.545 | 14 DAY | 1.8 | 5.8 | 15.0 | 6.3 | 7.5 | 5.0 |
| | ALIETTE ™ | WDG 80 | 8.712 | 14 DAY | | | | | | |
| 04 | NCAD 1 | SG 100 | 0.545 | 14 DAY | 1.3 | 6.3 | 7.5 | 6.8 | 7.8 | 0 |
| | MANCOZEB | WDG 80 | 17.43 | 14 DAY | | | | | | |
| 05 | NCAD 1 | SG 100 | 0.545 | 14 DAY | 5.5 | 7.0 | 2.5 | 7.3 | 6.8 | 0 |
| | MANCOZEB | WDG 80 | 17.43 | 14 DAY | | | | | | |
| | ALIETTE ™ | WDG 80 | 8.712 | 14 DAY | | | | | | |
| 06 | ALIETTE ™ | WDG 80 | 8.712 | 14 DAY | 2.5 | 5.3 | 16.3 | 6.0 | 6.3 | 25 |
| 07 | MANCOZEB | WDG 80 | 17.43 | 14 DAY | 2.0 | 6.0 | 13.8 | 6.5 | 6.8 | 8.8 |
| 08 | ALIETTE ™ | WDG 80 | 8.712 | 14 DAY | 1.0 | 7.8 | 0 | 8.0 | 8.0 | 0 |
| | FORE ™ | WP 80 ™ | 17.43 | 14 DAY | | | | | | |
| 09 | EXP10622 | WDG 80 | 8.712 | 14 DAY | 15 | 5.8 | 10.0 | 6.5 | 6.8 | 6.3 |

TABLE 2-continued

| ALIETTE ™/FORE ™ Interaction | | | | | | | | | | |
|---|---|---|---|---|---|---|---|---|---|---|
| Trt. | Pesticide | | | Application | Phyto | Turf | % Brown | Turf | Turf | % Brown |
| No. | Name | Formu. | LBai/A | Type | rating | Qual. | Patch | Qual. | Color | Patch |
| 10 | EXP10622 | WDG 80 | 8.712 | 14 DAY | 3.3 | 7.5 | 0 | 8.0 | 7.5 | 0 |
| | MANCOZEB | WP 80 ™ | 17.43 | 14 DAY | | | | | | |
| | LDS (0.05) = | | | | .8 | 1.0 | 9.4 | .6 | 1.0 | 6.8 |
| | STANDARD DEVIATION = | | | | .6 | .7 | 6.5 | .4 | .7 | 4.7 |
| | COEFF. OF VARIABILITY = | | | | 27.2 | 11.0 | 58.4 | 5.9 | 9.4 | 87.3 |

Table 3 is a comparative study of the effects of different formulations of mancozeb. The formulations of FORE™ WP80™ and FL4.0™, which contain mancozeb +Pigment Blue 15. gave better turf quality and turf color than other formulations of mancozeb without the Pigment Blue 15. Treatment #7 of ALIETTE™+FORE™FL4.0+BLENDEX™ (a blending agent) gave better results. Treatment #7 contains more Pigment Blue 25 than treatment #2.

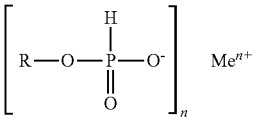

TABLE 3

| ALIETTE ™/MANCOZEB Interactions | | | | | | | | | | | | | | | | |
|---|---|---|---|---|---|---|---|---|---|---|---|---|---|---|---|---|
| Trt. | Pesticide | | | Application | Turf Quality | Turf Color | % Brown Patch | Turf Quality | Turf Color | % Brown Patch | Turf Quality | Turf Color | % Brown Patch | Turf Quality | Turf Color |
| No. | Name | Formu. | LBai/A | Type | | | | | | | | | | | |
| 01 | CONTROL | — | — | — | 3.8 | 4.5 | 60.0 | 3.3 | 4.0 | 67.5 | 2.8 | 3.8 | 75.0 | 4.8 | 6.3 |
| 02 | ALIETTE ™ | WDG 80 | 8.712 | 14 DAY | 7.0 | 7.0 | 10.0 | 7.8 | 7.5 | 5.0 | 7.3 | 7.0 | 5.0 | 7.0 | 6.8 |
| | FORE ™ | WP 80 | 17.42 | 14 DAY | | | | | | | | | | | |
| 03 | ALIETTE ™ | WDG 80 | 8.712 | 14 DAY | 6.0 | 6.3 | 12.5 | 6.0 | 6.0 | 1.3 | 6.0 | 6.0 | 8.8 | 5.8 | 53 |
| | LESCO MN | DG 80 | 17.42 | 14 DAY | | | | | | | | | | | |
| 04 | ALIETTE ™ | WDG 80 | 8.712 | 14 DAY | 6.3 | 6.5 | 13.8 | 6.0 | 6.0 | 2.5 | 6.0 | 6.3 | 12.5 | 6.0 | 5.5 |
| | PENCOZES | DF 75 | 17.42 | 14 DAY | | | | | | | | | | | |
| 05 | ALIETTE ™ | WDG 80 | 8.712 | 14 DAY | 6.0 | 6.5 | 11.3 | 6.3 | 6.3 | 5.0 | 6.3 | 6.3 | 8.8 | 5.8 | 5.3 |
| | PROTECT | DG 80 | 17.42 | 14 DAY | | | | | | | | | | | |
| 06 | ALIETTE ™ | WDG 80 | 8.712 | 14 DAY | 6.8 | 7.0 | 6.3 | 6.8 | 6.8 | 7.5 | 7.3 | 7.8 | 3.8 | 7.5 | 7.5 |
| | FORE ™ | F1 4.0 ™ | 17.42 | 14 DAY | | | | | | | | | | | |
| 07 | ALIETTE ™ | WDG 80 | 8.712 | 14 DAY | 7.0 | 7.3 | 5.0 | 8.5 | 7.8 | 0 | 8.0 | 8.0 | 1.3 | 8.0 | 8.0 |
| | FORE ™ | F1 4.0 ™ | 17.42 | 14 DAY | | | | | | | | | | | |
| | BLENDEX | % C | | 14 DAY | | | | | | | | | | | |
| 08 | ALIETTE ™ | WDG 80 | 8.712 | 14 DAY | 4.3 | 4.8 | 46.3 | 5.8 | 6.0 | 2.5 | 5.8 | 5.8 | 17.5 | 6.0 | 5.5 |
| | DITHANE | WDG 75 | 17.42 | 14 DAY | | | | | | | | | | | |
| 09 | LESCO MN | DG 80 | 17.42 | 14 DAY | 4.8 | 5.5 | 21.3 | 5.0 | 5.3 | 8.8 | 4.8 | 4.8 | 22.5 | 5.8 | 6.0 |
| | LDS (0.05) = | | | | 1.0 | .7 | 21.3 | .5 | .7 | 10.3 | .7 | .6 | 9.1 | .7 | 1.1 |
| | STANDARD DEVIATION = | | | | .7 | .5 | 14.6 | .4 | .5 | 7.0 | .5 | .4 | 6.2 | .5 | .7 |
| | COEFF. OF VARIABILITY = | | | | 11.7 | 8.3 | 70.6 | 5.8 | 7.4 | 63.3 | 8.5 | 6.6 | 36.1 | 7.6 | 11.6 |

Overall, the results indicate that the combination of ALIETTE™+FORE™. containing the Pigment Blue 15. provides a better improvement in turf quality and color over other combinations of ALIETTE™ and mancozeb without the Pigment Blue 15. The results demonstrate that the presence of the Pigment Blue 15, enhances the activity of the ALIETTE™ and mancozeb in a synergistic interaction.

The foregoing is illustrative of the present invention and is not to be construed as limiting thereof. The invention is defined by the following claims, with equivalents of the claims to be included therein.

That which is claimed is:

1. A method of combatting fungi and enhancing turf quality in turfgrass which comprises applying to said turfgrass synergistic fungicidally effective amounts of:

(a) a first active agent selected from the group consisting of (i) 1 part by weight of a monoester salt of a phosphorous acid of Formula (I):

wherein:

R is an alkyl radical having 2 to 4 carbon atoms,

Me is an alkali metal, alkaline earth, or aluminum atom, and n is a whole number from 1 to 3 equal to the valence of Me; and (ii) phosphorous acid or an alkali or alkali earth metal salt thereof; and (b) from 0.01 to 0.1 parts by weight of a phthalocyanine compound,

*wherein said method does not include the application of an ethylenebisdithiocarbamate contact fungicide*.

2. The method according to claim 1, wherein said step of applying comprises applying 1 part by weight of said first active agent, and 0.05 parts by weight of said phthalocyanine compound.

3. The method according claim 1, wherein said phthalocyanine compound is Pigment Blue 15.

4. The method according to claim 1, wherein said phthalocyanine compound is not Pigment Blue 15.

5. The method according to claim 1, wherein said step of applying is carried out by applying said first active agent and said phthalocyanine compound to said turfgrass together in a common carrier.

6. The method according to claim 1, wherein said turfgrass is bentgrass.

7. The method according to claim 1, wherein said turfgrass is bermudagrass.

8. The method according to claim 1, wherein said first active agent is applied to said turfgrass in an amount of from about 8 to about 16 pounds active ingredient per acre, and said phthalocyanine compound is applied to said turfgrass in an amount of from about 0.2 to about 0.8 pounds per acre.

[9. The method according to claim 1 consisting essentially of applying to said turfgrass, said first active agent in an amount of from about 8 to about 16 pounds active ingredient per acre, and said phthalocyanine compound in an amount of from about 0.2 to about 0.8 pounds per acre.]

10. A fungicidal composition [tier] *for* enhancing turf quality [which comprises] *wherein the active material present in* synergistic fungicidally effective amounts [of an active material comprising] *consists essentially of*:

(a) 1 part by weight of a first active agent selected from the group consisting of (i) a monoester salt of a phosphorous acid of Formula (I):

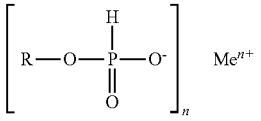

wherein:

R is an alkyl radical having 2 to 4 carbon atoms,

Me is an alkali metal, alkaline earth, or aluminum atom, and n is a whole number from 1 to 3 equal to the valence of Me; and (ii) phosphorous acid or an alkali or alkali earth metal salt thereof; and (b) from 0.01 to 0.1 parts by weight of a phthalocyanine compound

*wherein the composition does not include an ethylenebisdithiocarbamate contact fungicide.*

11. The composition according to claim 10, wherein said first active agent is said monoester salt of phosphorous acid, and R is selected from the group consisting of ethyl, propyl, and butyl.

12. The composition according to claim 10, wherein said first active agent is said monoester salt of phosphorous acid, and Me is selected from the group consisting of aluminum, calcium, magnesium, and sodium.

13. The composition according to claim 10, wherein said first active agent is said monoester salt of phosphorous acid, and said compound of Formula (I) is selected from the group consisting of calcium ethyl phosphite, sodium ethyl phosphite, aluminum ethyl phosphite, magnesium isopropyl phosphite, calcium isopropyl phosphite, aluminum isopropyl phosphite, magnesium ethyl phosphite, magnesium isobutyl phosphite, magnesium sec-butyl phosphite, calcium isobutyl phosphite, aluminum N-butyl phosphite, aluminum sec-butyl phosphite, and aluminum isobutyl phosphite.

14. The composition according to claim 10, wherein said first active agent is said monoester of phosphorous acid, and said compound of Formula (I) is aluminum ethyl phosphite.

15. The composition according to claim 10, wherein said phthalocyanine compound is selected from the group consisting of Pigment Blue 16, Vat Blue 29, Pigment Blue 15, Heliogen Green GG. Ingrain Blue 14, Ingrain Blue 5, Ingrain Blue 1, Pigment Green 37, and Pigment Green 7.

16. The composition according to claim 10, wherein said phthalocyanine compound is Pigment Blue 15.

17. The composition according to claim 14, wherein said phthalocyanine compound is not Pigment Blue 15.

[18. The composition according to claim 10, comprising 1 part by weight of said first active agent and between about 0.01 and about 0.1 parts by weight of said phthalocyanine compound.]

[19. The composition according to claim 10, consisting essentially of 1 part by weight of said first active agent and between about 0.01 and about 0.1 parts by weight of said phthalocyanine compound.]

20. The composition according to claim 10, wherein said composition is an aqueous suspension.

21. The composition according to claim 10, wherein said composition is a wettable powder.

22. The method according to claim 1, wherein said first active agent comprises ethyl aluminum phosphite and said phthalocyanine compound comprises Pigment Blue 15.

23. The composition according to claim 10, wherein said first active agent comprises ethyl aluminum phosphite and said phthalocyanine compound comprises Pigment Blue 15.

*24. A method of combatting fungi and enhancing turf quality in turfgrass which comprises applying to said turfgrass synergistic fungicidally effective amounts of:*

*(a) 1 part by weight of a first active agent selected the group consisting of phosphorous acid or an alkali or alkali earth metal salt thereof; and*

*(b) from 0.01 to 0.1 parts by weight of a phthalocyanine compound,*

*wherein said method does not include the application of an ethylenebisdithiocarbamate contact fungicide.*

*25. The method according to claim 24, wherein said step of applying comprises applying 1 part by weight of said first active agent, and 0.05 parts by weight of said phthalocyanine compound.*

*26. The method according claim 24, wherein said phthalocyanine compound is Pigment Blue 15.*

*27. The method according to claim 24, wherein said phthalocyanine compound is not Pigment Blue 15.*

*28. The method according to claim 24, wherein said step of applying is carried out by applying said first active agent and said phthalocyanine compound to said turfgrass together in a common carrier.*

*29. The method according to claim 24, wherein said turfgrass is bentgrass.*

*30. The method according to claim 24, wherein said turfgrass is bermudagrass.*

*31. The method according to claim 24, wherein said first active agent is applied to said turfgrass in an amount of from about 8 to about 16 pounds active ingredient per acre, and said phthalocyanine compound is applied to said turfgrass in an amount of from about 0.2 to about 0.8 pounds per acre.*

*32. A fungicidal composition for enhancing turf quality wherein the active material present in synergistic fungicidally effective amounts consists essentially of:*

*(a) 1 part by weight of a first active agent selected from the group consisting of phosphorous acid or an alkali or alkali earth metal salt thereof; and*

*(b) from 0.01 to 0.1 parts by weight of a phthalocyanine compound, and*

*wherein the composition does not include an ethylenebis-dithiocarbamate contact fungicide.*

*33. The composition according to claim 32, wherein said phthalocyanine compound is selected from the group consisting of Pigment Blue 16, Vat Blue 29, Pigment Blue 15, Heliogen Green GG, Ingrain Blue 14, Ingrain Blue 5, Ingrain Blue 1, Pigment Green 37, and Pigment Green 7.*

*34. The composition according to claim 32, wherein said phthalocyanine compound is Pigment Blue 15.*

*35. The composition according to claim 32, wherein said phthalocyanine compound is not Pigment Blue 15.*

*36. The composition according to claim 32, wherein said composition is an aqueous suspension.*

*37. The composition according to claim 32, wherein said composition is a wettable powder.*

* * * * *